(12) United States Patent
Hiller, Jr.

(10) Patent No.: US 11,813,228 B2
(45) Date of Patent: Nov. 14, 2023

(54) STABILIZATION DEVICES FOR USE WITH LOW-PROFILE FEEDING DEVICES AND RELATED METHODS OF USING THE SAME

(71) Applicant: Refined Medical Solutions LLC, Pennsauken, NJ (US)

(72) Inventor: Dennis F. Hiller, Jr., Pennsauken, NJ (US)

(73) Assignee: Refined Medical Solutions LLC, Pennsauken, NJ (US)

( * ) Notice: Subject to any disclaimer, the term of this patent is extended or adjusted under 35 U.S.C. 154(b) by 177 days.

(21) Appl. No.: 17/182,431

(22) Filed: Feb. 23, 2021

(65) Prior Publication Data
US 2021/0259926 A1   Aug. 26, 2021

Related U.S. Application Data

(60) Provisional application No. 62/981,207, filed on Feb. 25, 2020.

(51) Int. Cl.
*A61J 15/00* (2006.01)
(52) U.S. Cl.
CPC ....... *A61J 15/0053* (2013.01); *A61J 15/0049* (2013.01)
(58) Field of Classification Search
CPC ................ A61J 15/0053; A61J 15/0049; A61J 15/0057; A61J 15/0042; A61M 2039/0255; A61M 2039/085; A61M 2039/0276
See application file for complete search history.

(56) References Cited

U.S. PATENT DOCUMENTS

| 4,699,616 A | 10/1987 | Nowak et al. |
| 4,717,385 A | 1/1988 | Cameron et al. |
| 4,834,712 A | 5/1989 | Quinn et al. |
| 4,976,698 A | 12/1990 | Stokley |

(Continued)

FOREIGN PATENT DOCUMENTS

| WO | 02/066108 A1 | 8/2002 |
| WO | 2019/199829 A1 | 10/2019 |
| WO | 2021/173527 A1 | 9/2021 |

OTHER PUBLICATIONS

International Searching Authority (ISA/US). International Search Report and Written Opinion, issued in Application No. PCT/US2021/019192, dated May 21, 2021. 10 pages.

*Primary Examiner* — Lauren P Farrar
(74) *Attorney, Agent, or Firm* — Meunier Carlin & Curfman LLC

(57) ABSTRACT

A stabilization device for a low-profile feeding device may include a pad and a stabilizer body. The low-profile feeding device may have a tube, an external bolster, and an internal bolster. The pad may include an opening extending from a top surface to a bottom surface thereof and configured for receiving the tube therethrough. The stabilizer body may be fixedly attached to the top surface of the pad and configured for extending over the external bolster. The stabilizer body may include a cavity configured for receiving a base portion of the external bolster therein, an opening extending from the cavity to a top surface of the stabilizer body and configured for allowing access to an access port of the external bolster, and a slit extending from the top surface toward a bottom surface of the stabilizer body and from the opening to a first end of the stabilizer body.

15 Claims, 7 Drawing Sheets

(56) References Cited

U.S. PATENT DOCUMENTS

| | | |
|---|---|---|
| 5,073,170 A | 12/1991 | Schneider |
| 5,346,479 A | 9/1994 | Schneider |
| 5,451,212 A | 9/1995 | Andersen |
| 6,019,746 A | 2/2000 | Picha et al. |
| 6,375,639 B1 | 4/2002 | Duplessie et al. |
| 6,471,676 B1 | 10/2002 | Delegge et al. |
| 8,282,606 B2 | 10/2012 | Bierman |
| D864,384 S | 10/2019 | Parkhurst |
| 2003/0032932 A1 | 2/2003 | Stout |
| 2004/0024363 A1* | 2/2004 | Goldberg ............ A61J 15/0015 604/104 |
| 2008/0249476 A1 | 10/2008 | Bierman et al. |
| 2008/0319397 A1* | 12/2008 | Macaluso ............ A61J 15/0061 604/174 |
| 2009/0137961 A1 | 5/2009 | Bracken |
| 2010/0114034 A1 | 5/2010 | Wright et al. |
| 2011/0060295 A1* | 3/2011 | Hen .................... A61K 9/0014 604/290 |
| 2011/0288489 A1 | 11/2011 | Bierman et al. |
| 2012/0197191 A1* | 8/2012 | DeLegge ............ A61J 15/0061 604/99.04 |
| 2013/0165862 A1 | 6/2013 | Griffith et al. |
| 2016/0106958 A1* | 4/2016 | Price ...................... A61L 29/00 604/179 |
| 2020/0146944 A1 | 5/2020 | Moulton et al. |

* cited by examiner

STABILIZATION DEVICES FOR USE WITH LOW-PROFILE FEEDING DEVICES AND RELATED METHODS OF USING THE SAME

CROSS-REFERENCE TO RELATED APPLICATIONS

This application claims priority to and the benefit of U.S. Provisional Patent Application No. 62/981,207, filed on Feb. 25, 2020, the disclosure of which is expressly incorporated herein by reference in its entirety.

FIELD OF THE DISCLOSURE

The present disclosure relates generally to feeding tube assemblies for delivering fluids into and/or venting fluids from a patient and more particularly to stabilization devices for use with low-profile feeding devices and related methods of using the same.

BACKGROUND OF THE DISCLOSURE

Various types of feeding devices may be used for delivering fluids (i.e., liquids or gases) into and/or venting fluids from a patient. For example, such feeding devices may be used to deliver nutrition or medication to the stomach or small intestine of the patient. Additionally, or alternatively, such feeding devices may be used to vent gases or liquids from the stomach or small intestine of the patient. Different types of feeding devices have been developed, including gastrostomy tubes (G-tubes), jejunostomy tubes (J-tubes), and gastrojejunostomy tubes (GJ-tubes), with each type being configured to accommodate a desired placement with respect to the patient and to facilitate communication between a target site within the patient and an access point outside of the patient. Placement of such feeding devices generally may be achieved by forming a stoma in the stomach or intestinal wall and inserting the feeding device through the stoma such that a distal portion of the device is positioned at the target site while a proximal portion of the device remains outside of the patient for access. In an effort to minimize the amount of material exposed outside of the patient's body and potential complications caused by contact therewith, "low-profile" feeding devices have been developed.

A low-profile feeding device generally may include a tube, an external bolster attached to a proximal end portion of the tube, and an internal bolster attached to the tube and spaced apart from the external bolster. The tube may be configured for extending through the stoma and may include a primary lumen to facilitate delivery of fluids into the patient and/or venting of fluids from the patient. The external bolster may be configured for abutting the patient's abdominal wall and remaining outside of the patient during use of the device. The external bolster may include an access port in fluid communication with the primary lumen, which may allow for removable attachment of a feeding assembly or a venting assembly, when needed. The internal bolster may be configured for abutting the anterior wall of the patient's stomach or intestine and remaining in such location throughout a duration of use of the device. The internal bolster may include an expandable structure, such as an inflatable balloon, configured for inhibiting undesirable dislodgment of the device. When an inflatable balloon is used, the external bolster may include an inflation port, and a secondary lumen may extend through the tube from the inflation port to the balloon.

Although existing low-profile feeding devices generally may be suitable for delivering fluids into and/or venting fluids from a patient, their use may present certain problems associated with maintaining the desired placement of the device throughout a period of use. In many, instances, adhesive tape or pads may be placed over or around portions of an external bolster for post-operative stabilization of a feeding device to promote healing of tissue at the gastrostomy site. However, such techniques may be inadequate to prevent "rocking" of the feeding device relative to the patient, which may lead to widening of the gastrostomy site. In addition to being painful to the patient, such widening of the gastrostomy site may allow undesirable leakage of gastric secretions and feeds, which may increase skin breakdown or facilitate dislodgment of the feeding device. Dislodgment of a feeding device may present a significant patient safety concern. For example, movement of the internal bolster out of the stomach may cause feeds and medication to enter the peritoneal space, which typically leads to infection or sepsis and may cause death. Potential issues associated with use of low-profile feeding devices may be particularly problematic for pediatric patients. For example, existing skin appliances may be too large for use with pediatric patients, and adhesive residue from tape may be bothersome. Additionally, contact between the patient's skin and adjacent portions of the external bolster may lead to skin irritation. Further, connectors used with feeding or venting assemblies may cause the feeding device to be pulled to one side, thereby widening the gastrostomy site. Finally, use of low-profile feeding devices with pediatric patients may present increased incidence of hypergranulation (i.e., overgrowth of normal healing process) of tissue surrounding the gastrostomy site as well as keyholing of the gastrostomy site.

A need therefore exists for improved devices and methods for stabilizing feeding devices, such as low-profile feeding devices, relative to a patient, which may overcome one or more of the above-mentioned problems associated with existing feeding devices and their use.

SUMMARY OF THE DISCLOSURE

The present disclosure provides feeding tube assemblies and stabilization devices and related methods of using the same with respect to a patient. In one aspect, a feeding tube assembly for delivering fluids into a patient is provided. In one embodiment, the feeding tube assembly may include a pad, a low-profile: feeding device, and a stabilizer body. The pad may be configured for attaching to the patient. The pad may include an opening extending from a top surface to a bottom surface of the pad. The low-profile feeding device may include a tube, an external bolster, and an internal bolster. The tube may extend through the opening of the pad. The tube may include a primary lumen. The external bolster may be fixedly attached to a proximal end portion of the tube and disposed adjacent to the top surface of the pad. The external bolster may include an access port disposed along a top surface of the external bolster and in fluid communication with the primary lumen of the tube. The internal bolster may be fixedly attached to the tube and spaced apart from the external bolster. The stabilizer body may be fixedly attached to the top surface of the pad and may extend over the external bolster. The stabilizer body may include a cavity, an opening, and a slit. The cavity may receive a base portion of the external bolster therein. The opening may extend from the cavity to a top surface of the stabilizer body and may be configured for allowing access to the access port. The slit may extend from the top surface toward a bottom surface of the stabilizer body and from the opening to a first end of the stabilizer body.

In some embodiments, the pad may include an adhesive disposed on the bottom surface of the pad and configured for attaching the pad to the patient. In some embodiments, the pad may include a slit extending from the top surface to the bottom surface of the pad and from the opening to an outer periphery of the pad. In some embodiments, the slit of the stabilizer body may be aligned with the slit of the pad. In some embodiments, the stabilizer body may be fixedly attached to the pad by an adhesive. In some embodiments, the external bolster may include a tether and a plug. The tether may extend away from the access port and through a recess of the stabilizer body. The plug may be fixedly attached to the tether and configured for removably engaging the access port through the opening of the stabilizer body. In some embodiments, the tether may have a rectangular cross-sectional shape, and the recess of the stabilizer body may have a rectangular cross-sectional shape. In some embodiments, the internal bolster may include an inflatable balloon, and the external bolster may include an inflation port extending away from the access port and through a recess of the stabilizer body. The inflation port may be in fluid communication with the balloon via a secondary lumen of the tube. In some embodiments, the inflation port may have a circular cross-sectional shape, and the recess of the stabilizer body may have a C-shaped cross-sectional shape.

In some embodiments, the cavity may extend from the bottom surface of the stabilizer body to the opening of the stabilizer body. In some embodiments, the stabilizer body may include a first recess receiving a first extension portion of the external bolster therein. The first recess may extend from the cavity. In some embodiments, the first recess may extend from the bottom surface of the stabilizer body toward the top surface of the stabilizer body. In some embodiments, the stabilizer body may include a second recess receiving a second extension portion of the external bolster therein. The second recess may extend from the cavity. In some embodiments, the second recess may extend from the bottom surface of the stabilizer body toward the top surface of the stabilizer body. In some embodiments, the first recess may extend from the cavity to the first end of the stabilizer body, and the second recess may extend from the cavity to an opposite second end of the stabilizer body. In some embodiments, the slit of the stabilizer body may extend from the first recess to the top surface of the stabilizer body. In some embodiments, portions of the stabilizer body adjacent the slit of the stabilizer body may be configured to be resiliently deformed from a natural state to a deformed state and to automatically return to the natural state.

In some embodiments, the stabilizer body may include a first window and a second window. The first window may extend from the cavity to a first side of the stabilizer body and may be configured for allowing visualization of an ostomy site of the patient. The first window may be spaced apart from the opening of the stabilizer body. The second window may extend from the cavity to an opposite second side of the stabilizer body and may be configured for allowing visualization of the ostomy site. The second window may be spaced apart from the opening of the stabilizer body. In some embodiments, the stabilizer body may include a first leg and a second leg. The first leg may extend along a first side of the stabilizer body and may be fixedly attached to the pad. The second leg may extend along an opposite second side of the stabilizer body and may be fixedly attached to the pad. The first leg and the second leg may be spaced apart from one another by the cavity. In some embodiments, the stabilizer body may include a cross member extending between the first leg and the second leg and over a portion of the external bolster. In some embodiments, the first leg, the second leg, and the cross member may be integrally formed with one another. In some embodiments, the stabilizer body may be formed of a polymeric material.

In another aspect, a stabilization device for inhibiting movement of a low-profile feeding device relative to a patient is provided. In one embodiment, the stabilization device may include a pad and a stabilizer body. The low-profile feeding device may have a tube, an external bolster, and an internal bolster. The pad may be configured for attaching to the patient. The pad may include an opening extending from a top surface to a bottom surface of the pad and configured for receiving the tube therethrough. The stabilizer body may be fixedly attached to the top surface of the pad and configured for extending over the external bolster. The stabilizer body may include a cavity, an opening, and a slit. The cavity may be configured for receiving a base portion of the external bolster therein. The opening may extend from the cavity to a top surface of the stabilizer body and be configured for allowing access to an access port of the external bolster. The slit may extend from the top surface toward a bottom surface of the stabilizer body and from the opening to a first end of the stabilizer body.

In some embodiments, the pad may include an adhesive disposed on the bottom surface of the pad and configured for attaching the pad to the patient. In some embodiments, the pad may include a slit extending from the top surface to the bottom surface of the pad and from the opening to an outer periphery of the pad. In some embodiments, the slit of the stabilizer body may be aligned with the slit of the pad. In some embodiments, the stabilizer body may be fixedly attached to the pad by an adhesive. In some embodiments, the stabilizer body may include a recess configured for receiving a tether of the external bolster therethrough, and the opening of the stabilizer body may be configured for receiving a plug of the external bolster therethrough. In some embodiments, the recess of the stabilizer body may have a rectangular cross-sectional shape. In some embodiments, the stabilizer body may include a recess configured for receiving an inflation port of the external bolster therethrough. In some embodiments, the recess of the stabilizer body may have a C-shaped cross-sectional shape.

In some embodiments, the cavity may extend from the bottom surface of the stabilizer body to the opening of the stabilizer body. In some embodiments, the stabilizer body may include a first recess configured for receiving a first extension portion of the external bolster therein. The first recess may extend from the cavity. In some embodiments, the first recess may extend from the bottom surface of the stabilizer body toward the top surface of the stabilizer body. In some embodiments, the stabilizer body may include a second recess configured for receiving a second extension portion of the external bolster therein. The second recess may extend from the cavity. In some embodiments, the second recess may extend from the bottom surface of the stabilizer body toward the top surface of the stabilizer body. In some embodiments, the first recess may extend from the cavity to the first end of the stabilizer body, and the second recess may extend from the cavity to an opposite second end of the stabilizer body. In some embodiments, the slit of the stabilizer body may extend from the first recess to the top surface of the stabilizer body. In some embodiments, portions of the stabilizer body adjacent the slit of the stabilizer body may be configured to be resiliently deformed from a natural state to a deformed state and to automatically return to the natural state.

In some embodiments, the stabilizer body may include a first window and a second window. The first window may extend from the cavity to a first side of the stabilizer body and may be configured for allowing visualization of an ostomy site of the patient. The first window may be spaced apart from the opening of the stabilizer body. The second window may extend from the cavity to an opposite second side of the stabilizer body and may be configured for allowing visualization of the ostomy site. The second window may be spaced apart from the opening of the stabilizer body. In some embodiments, the stabilizer body may include a first leg and a second leg. The first leg may extend along a first side of the stabilizer body and may be fixedly attached to the pad. The second leg may extend along an opposite second side of the stabilizer body and may be fixedly attached to the pad. The first leg and the second leg may be spaced apart from one another by the cavity. In some embodiments, the stabilizer body may include a cross member extending between the first leg and the second leg and configured for extending over a portion of the external bolster. In some embodiments, the first leg, the second leg, and the cross member may be integrally formed with one another. In some embodiments, the stabilizer body may be formed of a polymeric material.

These and other aspects and improvements of the present disclosure will become apparent to one of ordinary skill in the art upon review of the following detailed description when taken in conjunction with the several drawings and the appended claims.

Figure 1A:
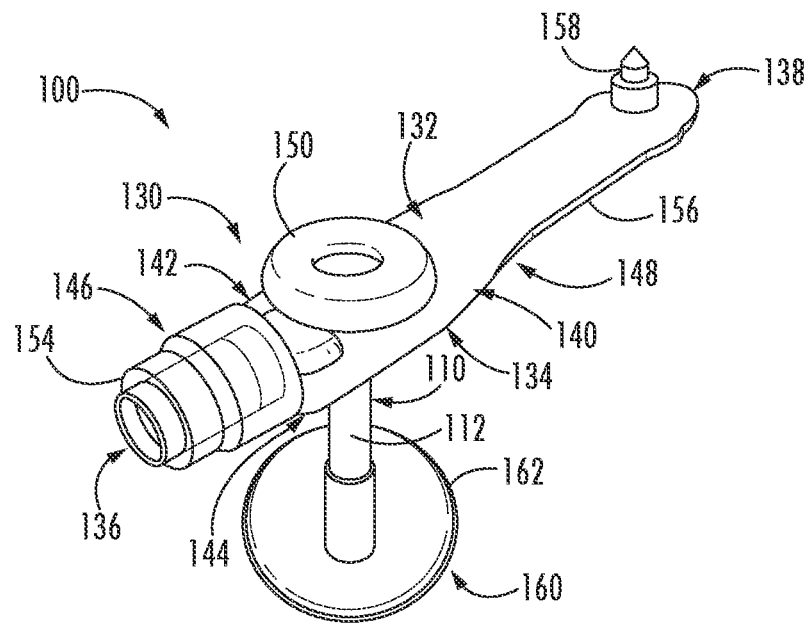
FIG. 1A is a top perspective view of an example low-profile feeding device, showing a tube, an external bolster, and an internal bolster of the low-profile feeding device.

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. The use of the same reference numerals indicates similar, but not necessarily the same or identical components. Different reference numerals may be used to identify similar components. Various embodiments may utilize elements or components other than those illustrated in the drawings, and some elements and/or components may not he present in various embodiments. The use of singular terminology to describe a component or element may, depending on the context, encompass a plural number of such components or elements and vice versa.

DETAILED DESCRIPTION OF THE DISCLOSURE

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, and components have not been described in detail so as not to unnecessarily obscure aspects of the embodiments.

Overview

Embodiments of stabilization devices and related methods of using such stabilization devices with feeding devices are provided. The stabilization devices may be used with a low-profile feeding device and together with the low-profile feeding device may form a feeding tube assembly. A low-profile feeding device generally may include a tube, an external holster attached to a proximal end portion of the tube, and an internal bolster attached to the tube and spaced apart from the external bolster. As discussed above, the use of low-profile feeding devices may present certain problems associated with maintaining desired placement of the device relative to the patient throughout a period of use. The stabilization devices described herein advantageously may be used to inhibit movement of a low-profile feeding device relative to a patient.

As described herein, a stabilization device may include a pad and a stabilizer body. The pad may be configured for attaching to a patient. The pad may include an opening extending from a top surface to a bottom surface of the pad and configured for receiving the tube of the low-profile feeding device therethrough. The stabilizer body may be fixedly attached to the top surface of the pad and configured for extending over the external bolster of the low-profile feeding device. In this manner, during use of the stabilization device, the pad may be attached to the patient, and at least a portion of the external bolster may be captured between the stabilizer body and the pad, thereby inhibiting movement of the low-profile feeding device relative to the patient. The stabilizer body may include a cavity and an opening. The cavity may be configured for receiving a base portion of the external bolster therein. The opening may extend from the cavity to a top surface of the stabilizer body and be configured for allowing access to an access port of the external bolster. In this manner, during use of the stabilization device, the access port may be accessible for attaching a feeding assembly or a venting assembly thereto while the stabilization device inhibits movement of the low-profile feeding device relative to the patient. Depending on the configuration of the low-profile feeding device, the stabilizer body also may include one or more recesses configured for receiving mating portions of the external bolster, such as a tethered plug or an inflation port thereof, while still allowing access to and use of such portions during use of the stabilization device. Respective shapes and arrangements of the cavity, opening, and recesses of the stabilizer body may be selected to correspond to shapes and arrangements of mating features of the external bolster, as described below.

Still other benefits and advantages of the stabilization devices provided herein over conventional devices and techniques will be appreciated by those of ordinary skill in the art from the following description and the appended drawings.

Low-Profile Feeding Devices

Figure 1B:
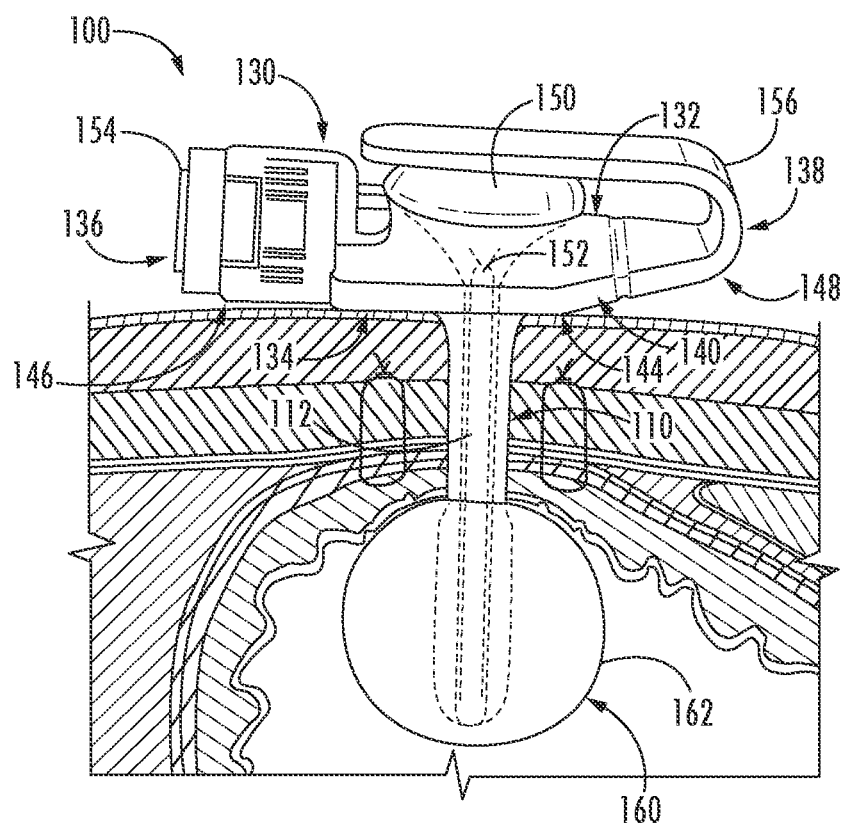
FIG. 1B is a side view of the low-profile feeding device of FIG. 1A, illustrating an example placement of the low-profile feeding device with respect to a patient.

Referring now to FIGS. 1A and 1B, an example low-profile feeding device 100 (which also may be referred to as an "enteral feeding device," a "feeding device," or simply a "device") is depicted. The feeding device 100 is configured for delivering fluids into and/or venting fluids from a patient. For example, the feeding device 100 may be used to deliver nutrition or medication to the stomach or small intestine of the patient. Additionally, or alternatively, the feeding device 100 may be used to vent gases or liquids from the stomach or small intestine of the patient. Various configurations of the feeding device 100 may be used. In some embodiments, the feeding device 100 may be provided as a G-tube. In some embodiments, the feeding device 100 may be provided as a J-tube. In some embodiments, the feeding device 100 may be provided as a GJ-tube.

The low-profile feeding device 100 generally may include a tube 110 configured for extending through a stoma formed in a patient, an external bolster 130 configured for abutting the patient's abdominal wall and remaining outside of the patient during use of the device 100, and an internal bolster 160 configured for abutting the anterior wall of the patient's stomach and remaining within the stomach during use of the device 100. An example placement of the feeding device 100 with respect to the anatomy of a patient is depicted in FIG. 1B. In other embodiments, the internal bolster 160 may be configured for abutting the anterior wall of the patient's intestine and remaining within the intestine during use of the device 100.

The tube 110 may include a primary lumen 112 to facilitate delivery of fluids into the patient and/or venting of fluids from the patient. In some embodiments, the primary lumen 112 may extend through the tube 110 from a proximal end to a distal end thereof. The external bolster 130 may be fixedly attached to the tube 110. In some embodiments, the external bolster 130 may be fixedly attached to a proximal end portion of the tube 110. The internal bolster 160 also may be fixedly attached to the tube 110 and spaced apart from the external bolster 130. In some embodiments, the internal bolster 160 may be fixedly attached to a distal end portion of the tube 110. In some embodiments, the tube 110 and the external bolster 130 may be integrally formed with one another. In sonic embodiments, the tube 110 and the internal bolster 160 may be integrally formed with one another. In some embodiments, the tube 110, the external bolster 130, and the internal bolster 160 may be separately formed and fixedly attached to one another.

As shown, the external bolster 130 may have a top surface 132, a bottom surface 134 disposed opposite the top surface 132 in a vertical direction, a first end 136, a second end 138 disposed opposite the first end 136 in a longitudinal direction, a first side 140, and a second side 142 disposed opposite the first side 140 in a lateral direction. In some embodiments, the external bolster 130 may include a base portion 144 that is fixedly attached to the tube 110 and one or more extension portions that are attached to and extend away from the base portion 144. For example, the external bolster 130 may include a first extension portion 146 and a second extension portion 148. In some embodiments, the first extension portion 146 and the second extension portion 148 may extend away from the base portion 144 in opposite directions, as shown, although other configurations of the extension portions 146, 148 may be used. In some embodiments, the first extension portion 146 and the second extension portion 148 may extend away from the base portion 144 in directions perpendicular to one another or forming other types of angled relationships. In some embodiments, the external bolster 130 may include four extension portions, which may be equally spaced apart from one another in a circumferential array or may have other arrangements. It will be appreciated that various configurations of the base portion 144 and extension portions of the external bolster 130 may be used, which may depend at least in part on functional requirements of the feeding device 100 (ex., depending on whether the device 100 is designed as a G-tube, a J-tube, a GJ-tube, or another type of feeding device).

The external bolster 130 may include one or more access ports that are accessible outside of the patient during use of the feeding device 100. The access port(s) may allow for removable attachment of a feeding assembly, a venting assembly, or other type of assembly for communicating with the device 100 when needed. For example, the access port(s) may be configured for removable attachment with such assemblies via one or more connectors thereof. As shown, the external bolster 130 may include an access port 150 that is in fluid communication with the primary lumen 112 of the tube 110. In some embodiments, the access port 150 may be disposed along the top surface 132 of the external bolster 130, although other arrangements of the access port 150 on the external bolster 130 may be used. In some embodiments, the external bolster 130 may include a valve 152 configured for controlling fluid flow between the access port 150 and the primary lumen 112. The valve 152 may be movable between a closed state that prevents or inhibits fluid flow and an open state that allows fluid flow. Various configurations of the valve 152 may be used. In some embodiments, the external bolster 130 may include two or more access ports. For example, when the feeding device 100 is provided as a GJ-tube, the external bolster 130 may include a first, gastric access port, and a second, jejunal access port. In such embodiments, the gastric access port may be in fluid communication with the primary lumen 112 for communicating with the patient's stomach, and the jejunal access port may he in fluid communication with a secondary lumen of the tube 110 for communicating with the patient's small intestine.

The internal bolster 160 may be configured for facilitating retention of the internal bolster 160 within the patient's stomach or intestine during use of the feeding device 100. In this manner, the internal bolster 160 may inhibit dislodgment of the feeding device 100. In some embodiments, the internal bolster 160 may include an expandable structure that is configured for transitioning between a compact configuration and an expanded configuration. The internal bolster 160 may be maintained in the compact configuration during insertion of the internal bolster 160 into the patient, transitioned to the expanded configuration once the internal bolster 160 is positioned within the stomach or intestine, and maintained in the expanded configuration during use of the feeding device 100. In some embodiments, as shown, the internal bolster 160 may include an inflatable balloon 162 that is configured for transitioning between a deflated, compact configuration and an inflated, expanded configuration. When in the expanded configuration, as shown in FIGS. 1A and 1B, a lateral dimension (e.g., diameter) of the balloon 162 may be greater than a lateral dimension (e.g., diameter) of the tube 110 to facilitate retention of the internal bolster 160 within the patient's stomach or intestine. In some embodiments, the internal bolster 160 may include an expandable button or bumper that is configured for transitioning between a compact configuration and an expanded configuration to facilitate retention of the internal bolster 160 in a similar manner. In some embodiments, the internal bolster 160 may include a non-expandable member, such as a button or bumper, that is flexible or otherwise shaped to ease insertion into the stomach or intestine and then facilitate retention of the internal bolster 160 therein. It will be appreciated that various configurations of the internal bolster 160 may be used.

In some embodiments, the one or more extension portions of the external bolster 130 may include an inflation port. For example, an inflation port may be provided when the internal bolster 160 includes an inflatable balloon, such as the balloon 162. According to the illustrated embodiment, the first extension portion 146 may include an inflation port 154 that is in fluid communication with the balloon 162 via a secondary lumen extending through the tube 110 from the inflation port 162 to the balloon 162. The inflation port 154 may allow for removable attachment of an inflation device, such as a syringe, for selectively inflating and deflating the balloon 162, when needed. In some embodiments, the external bolster 130 may include an inflation valve configured for controlling fluid flow between the inflation port 154 and the secondary lumen. The inflation valve may be movable between a closed state that prevents or inhibits fluid flow and an open state that allows fluid flow.

In some embodiments, the one or more extension portions of the external bolster 130 may include a tether having a plug fixedly attached thereto. The plug may be configured for removably engaging an access port of the external bolster 130 when the access port is not being used for delivering or removing fluids. According to the illustrated embodiment, the second extension portion 148 may include a tether 156 having a plug 158 fixedly attached thereto. The plug 158 may be configured for removably engaging the access port 150. The tether 156 may be provided as a flexible member configured for transitioning between a natural configuration (FIG. 1A) and a bent configuration (FIG. 1B). As shown, the tether 156 may be moved from the natural configuration to the bent configuration to allow the plug 158 to engage the access port 150, and the tether 156 may be moved from the bent configuration to the natural configuration when the plug 158 is removed from the access port 150. In some embodiments, two or more extension portions of the external bolster 130 each may include a tether having a plug fixedly attached thereto. For example, when the feeding device 100 is provided as a GJ-tube, the external bolster 130 may include a first tethered plug for removably engaging the gastric access port and a second tethered plug for removably engaging the jejunal access port.

In some embodiments, the one or more extension portions of the external bolster 130 may include one or more tabs extending away from the base portion 144. The tabs may be configured for limiting rocking of the feeding device 100 in a direction corresponding to the extent of the tab. In sonic embodiments, a tab may extend away from the base portion 144 in a direction opposite an extension portion having a different configuration, such as an inflation port or a tethered plug. In some embodiments, a tab may extend away from the base portion 144 in a direction perpendicular to the extent of an extension portion having a different configuration, such as an inflation port or a tethered plug. Various shapes, configurations, and arrangements of the tabs, if present, may be used for the external bolster 130.

Stabilization Devices and Feeding Tube Assemblies

FIGS. 2A-2L, illustrate an example feeding tube assembly 200 (which also may be referred to as an "enteral feeding tube assembly," a "feeding assembly," or simply an "assembly") and components thereof in accordance with one or more embodiments of the disclosure. As shown, the feeding tube assembly 200 may include a stabilization device 202 (which also may be referred to as a "stabilizer" or simply a "device") and the low-profile feeding device 100. Although the stabilization device 202 is depicted as being used with the low-profile feeding device 100, it will be appreciated that the stabilization device 202 may be used with other types of low-profile feeding devices in a similar manner. As described herein, the stabilization device 202 is configured for inhibiting relative movement of a low-profile feeding device, such as the low-profile feeding device 100, relative to a patient during use of the feeding device. In some embodiments, the stabilization device 202 and the low-profile feeding device may be provided separately and assembled to one another by a clinician to form the feeding tube assembly 200 just prior to use of the assembly 200 with a patient. In other embodiments, the stabilization device 202 and the low-profile feeding device may be preassembled to form the feeding tube assembly 200 for use by a clinician.

Figure 2A:
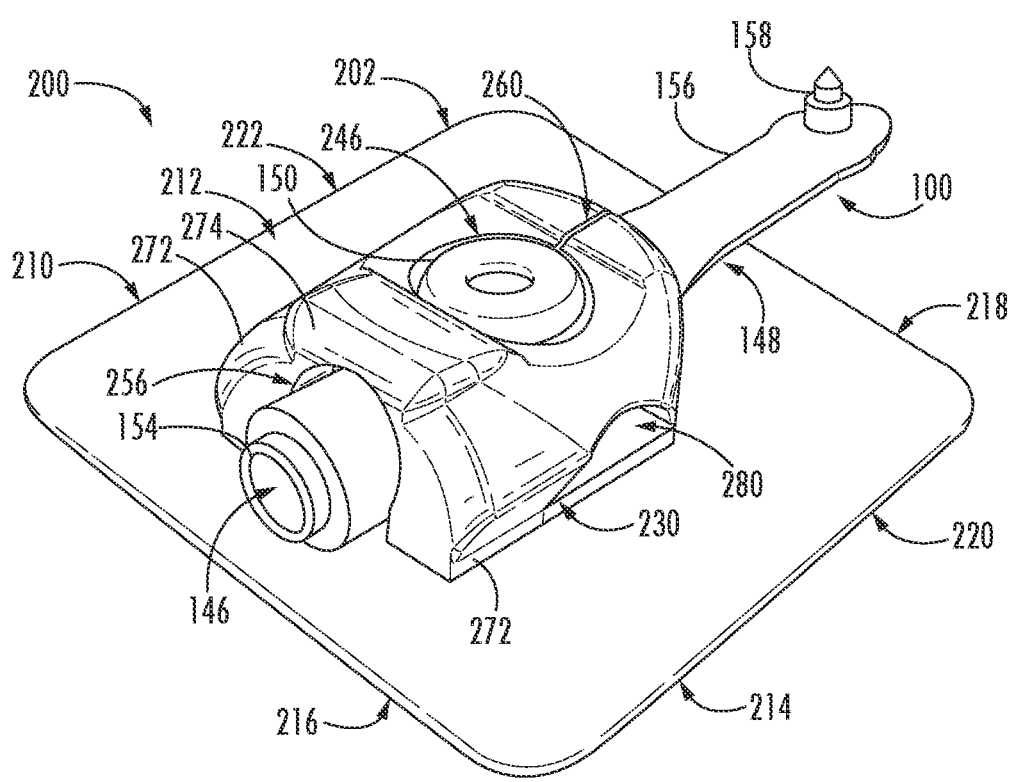
FIG. 2A is a top perspective view of an example feeding tube assembly in accordance with one or more embodiments of the disclosure, showing a low-profile feeding device and a stabilization device of the feeding tube assembly.
Figure 2B:
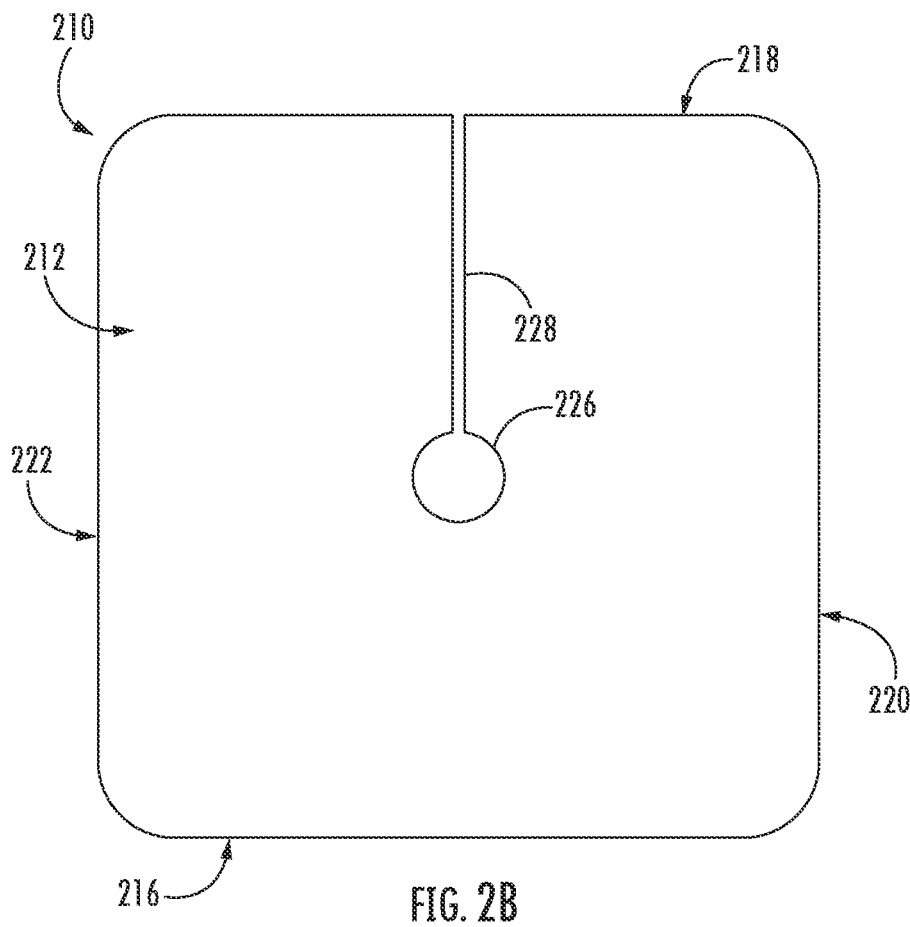
FIG. 2B is a top view of a pad of the stabilization device of FIG. 2A.
Figure 2C:
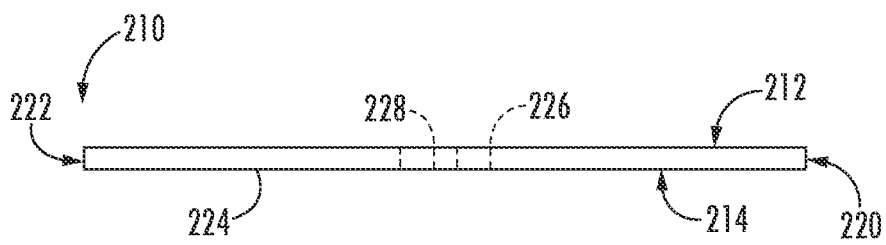
FIG. 2C is an end view of the pad of FIG. 2B.
Figure 2D:
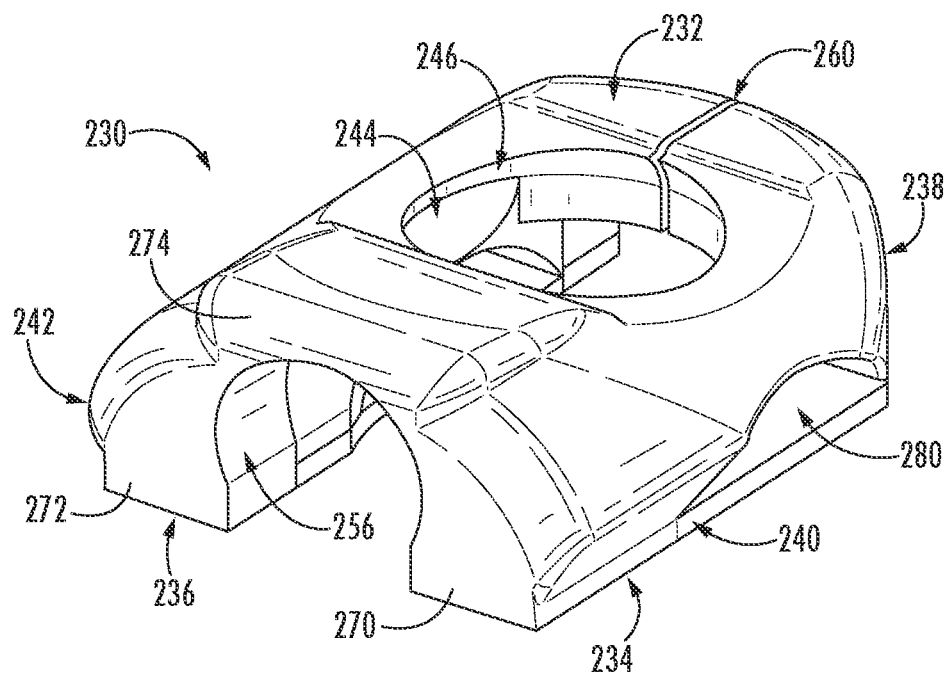
FIG. 2D is a top perspective view of a stabilizer body of the stabilization device of FIG. 2A.
Figure 2E:
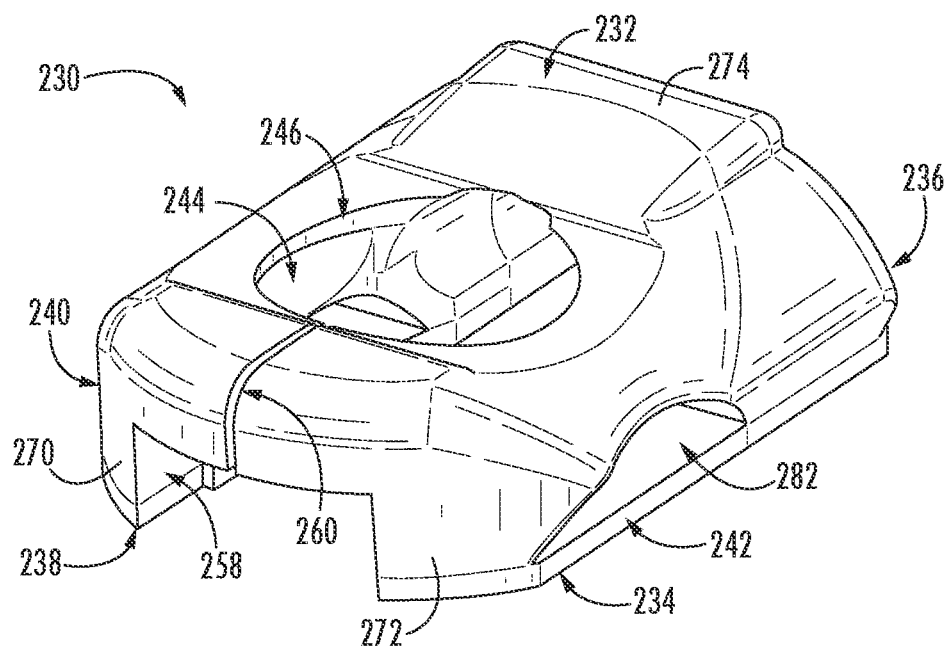
FIG. 2E is a top perspective view of the stabilizer body of FIG. 2D.
Figure 2F:
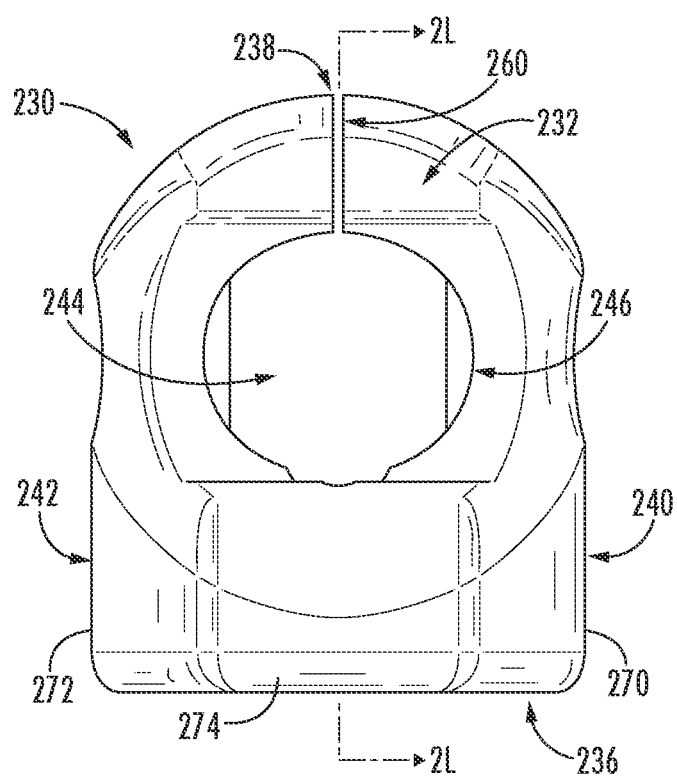
FIG. 2F is a top view of the stabilizer body of FIG. 2D.
Figure 2G:
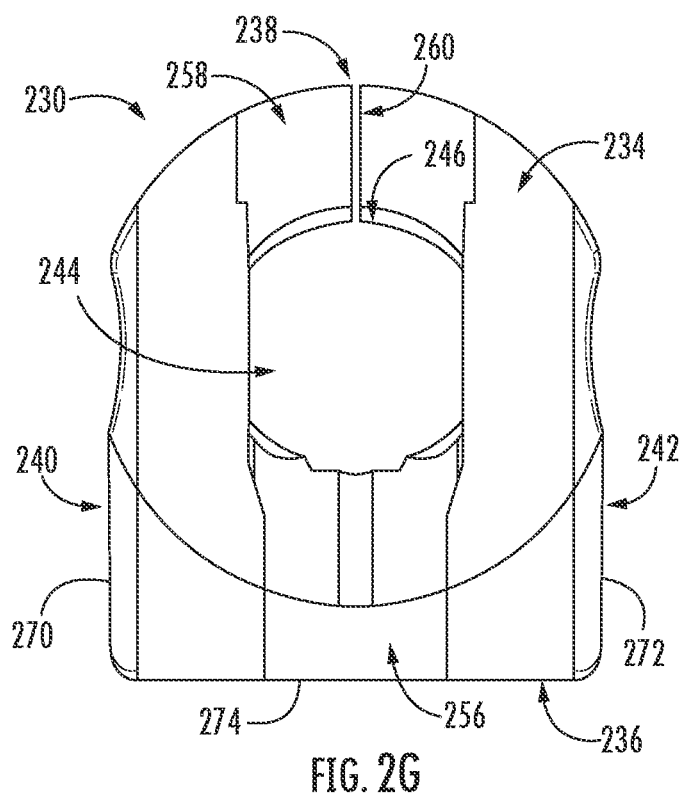
FIG. 2G is a bottom view of the stabilizer body of FIG. 2D.
Figure 2H:
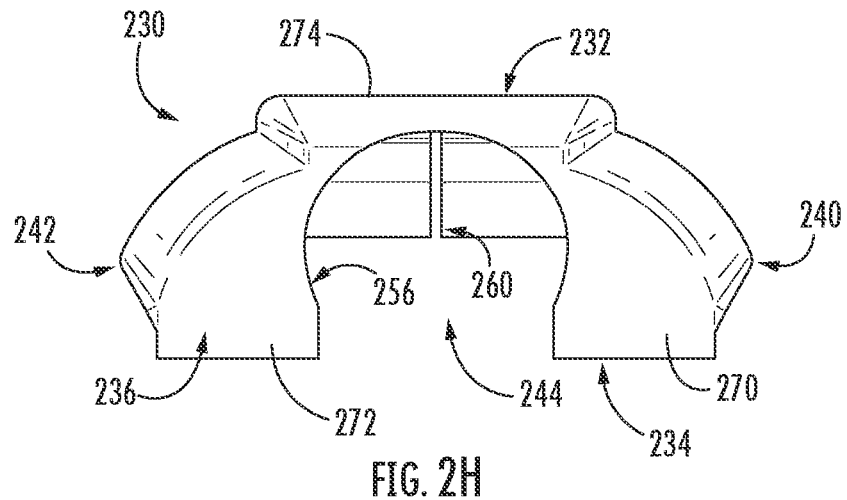
FIG. 2H is an end view of the stabilizer body of FIG. 2D.
Figure 2I:
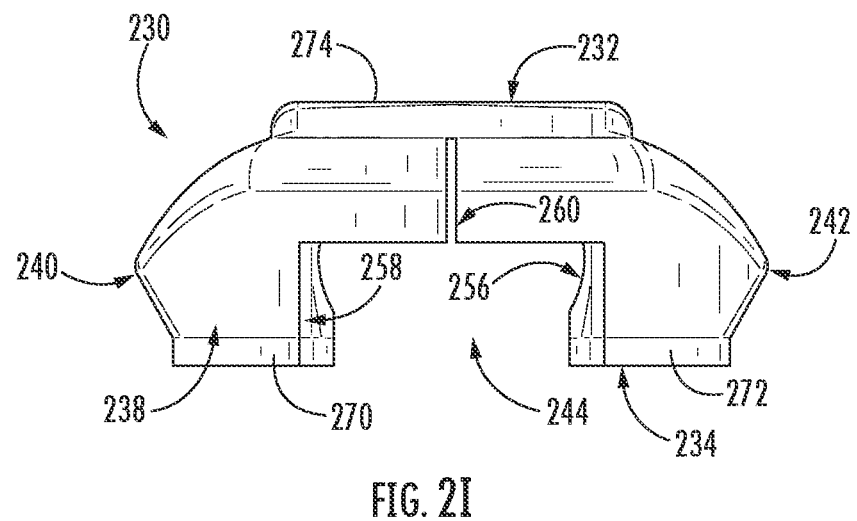
FIG. 2I is an opposite end view of the stabilizer body of FIG. 2D.
Figure 2J:
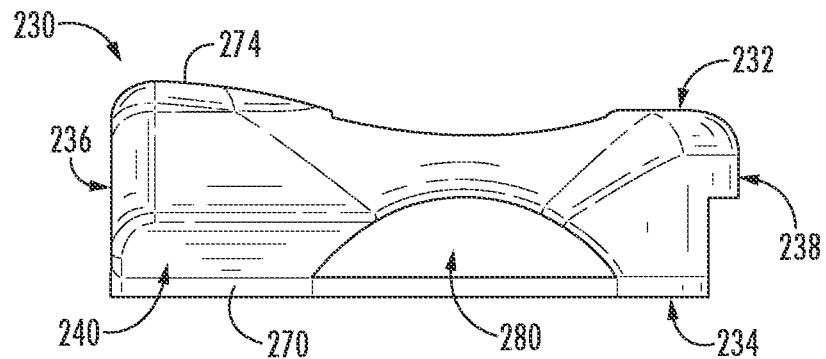
FIG. 2J is a side view of the stabilizer body of FIG. 2D.
Figure 2K:
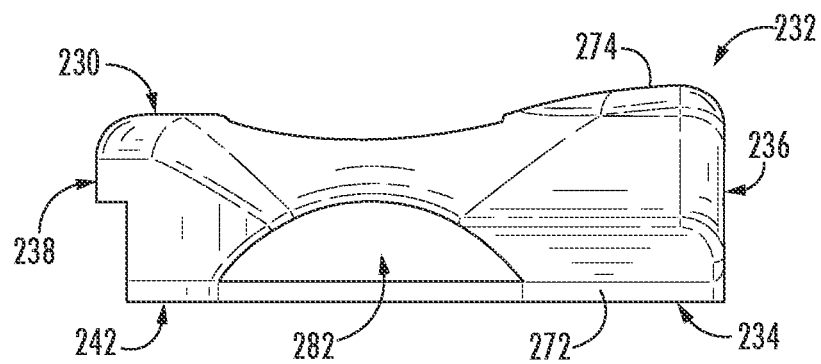
FIG. 2K is an opposite side view of the stabilizer body of FIG. 2D.
Figure 2L:
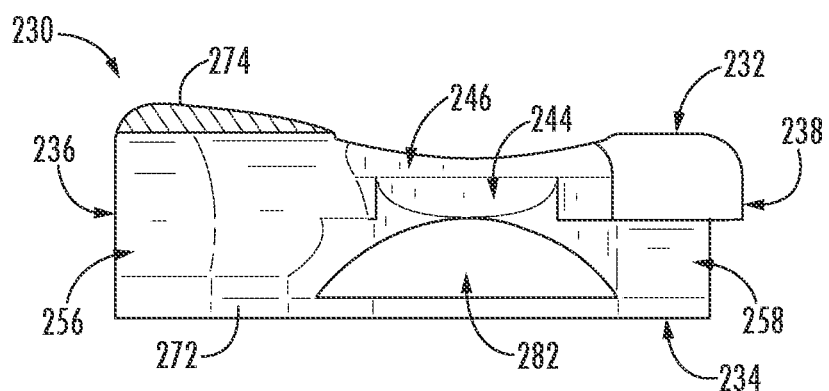
FIG. 2L is a cross-sectional side view of the stabilizer body of FIG. 2D, taken along line 2L-2L of FIG. 2F.

The stabilization device 202 may include a pad 210 and a stabilizer body 230. The pad 210 may be configured for attaching to a patient and may provide a base structure for the stabilizer body 230. As shown in FIGS. 2A-2C, the pad 210 may have a top surface 212, a bottom surface 214 disposed opposite the top surface 212 in a vertical direction, a first end 216, a second end 218 disposed opposite the first end 216 in a longitudinal direction, a first side 220, and a second side 222 disposed opposite the first side 220 in a lateral direction. The pad 210 may be formed as a flexible sheet-like member such that the pad 210 is adapted to conform to the shape of the patient's body when the pad 210 is applied thereto. In some embodiments, the pad 210 may include an adhesive 224 disposed on the bottom surface 214 of the pad 210 and configured for attaching the pad 210 to the patient. In other embodiments, alternative techniques for attaching the pad 210 to the patient may be used.

As shown, the pad 210 may include an opening 226 extending from the top surface 212 to the bottom surface 214 of the pad 210. The opening 226 may be configured for receiving the tube of the low-profile feeding device therethrough. For example, when the stabilization device 202 is used with the low-profile feeding device 100, the tube 110 may extend through the opening 226 of the pad 210. In some embodiments, the pad 210 may include a slit 228 adapted to ease assembly of the stabilization device 202 with the low-profile feeding device. The slit 228 may extend from the top surface 212 to the bottom surface 214 of the pad 210 and from the opening 226 to the outer periphery of the pad 210. For example, the slit 228 may extend from the opening 226 to the second end 218 of the pad 210, as shown, although other arrangements of the slit 228 may be used. During assembly, the slit 228 may allow the adjacent portions of the pad 210 to be separated from one another for positioning of the tube of the low-profile feeding device, such as the tube 110 of the feeding device 100, within the opening 226 of the pad 210. When the low-profile feeding device is assembled to the stabilization device 202, the external bolster, such as the external bolster 130 of the feeding device 110, may be disposed adjacent to the top surface 212 of the pad 210. It will be appreciated that the dimensions of the pad 210 as well as the opening 226 and the slit 228 thereof may be varied for different applications. Further, although the pad 210 is depicted as having a generally rectangular shape with rounded corners, it will be appreciated that different shapes of the pad 210 may be used.

The stabilizer body 230 may he fixedly attached to the pad 210. For example, the stabilizer body 230 may be fixedly attached to the top surface 212 of the pad 210, as shown in FIG. 2A. In some embodiments, the stabilizer body 230 may be fixedly attached to the pad 210 by an adhesive. In other embodiments, alternative techniques for attaching the stabilizer body 230 to the pad 210 may be used. As shown in FIGS. 2D-2L, the stabilizer body 230 may have a top surface 232, a bottom surface 234 disposed opposite the top surface 232 in a vertical direction, a first end 236, a second end 238 disposed opposite the first end 236 in a longitudinal direction, a first side 240, and a second side 242 disposed opposite the first side 240 in a lateral direction. The stabilizer body 230 may be configured for extending over the external bolster of the low-profile feeding device, such as the external bolster 130 of the feeding device 110, as shown in FIG. 2A. In this manner, during use of the stabilization device 202, the pad 210 may be attached to the patient, and at least a portion of the external bolster may be captured between the stabilizer body 230 and the pad 210, thereby inhibiting movement of the low-profile feeding device relative to the patient.

The stabilizer body 230 may include a cavity 244 and an opening 246. The cavity 244 may be configured for receiving the base portion of the external bolster therein. For example, when the stabilization device 202 is used with the low-profile feeding device 100, the base portion 144 of the external bolster 130 may be received within the cavity 244, as shown in FIG. 2A. The cavity 244 may extend from the bottom surface 234 of the stabilizer body 230 to the opening 246. The opening 246 may extend from the cavity 244 to the top surface 232 of the stabilizer body 230. The opening 246 may be configured for allowing access to the access port of the low-profile feeding device. For example, when the stabilization device 202 is used with the low-profile feeding device 100, the access port 150 of the external bolster 130 may be accessible through the opening 246, as shown in FIG. 2A. In this manner, during use of the stabilization device 202, the access port of the low-profile feeding device may be accessible for attaching a feeding assembly or a venting assembly thereto while the stabilization device 202 inhibits movement of the low-profile feeding device relative to the patient. Further, the opening 246 may be configured for allowing a tethered plug to removably engage the access port of the low-profile feeding device during use of the stabilization device 202. For example, when the stabilization device 202 is used with the low-profile feeding device 100, the plug 158 may be able to removably engage the access port 150 through the opening 246.

The stabilizer body 230 also may include one or more recesses configured for receiving mating portions, such as extension portions, of the external bolster of the low-profile feeding device. For example, the stabilizer body 230 may include a first recess 256 and a second recess 258. Each of the first recess 256 and the second recess 258 may extend from the cavity 244. In some embodiments, as shown, the first recess 256 may extend from the cavity 244 to the first end 236 of the stabilizer body 230, and the second recess 258 may extend from the cavity 244 to the second end 238 of the stabilizer body 230. Further, each of the first recess 256 and the second recess 258 may extend from the bottom surface 234 toward the top surface 232 of the stabilizer body 230. The first recess 256 may be configured for receiving a first extension portion of the external bolster therein, and the second recess 258 may be configured for receiving a second extension portion of the external bolster therein. For example, when the stabilization device 202 is used with the low-profile feeding device 100, part of the first extension portion 146 may be received within the first recess 256, and part of the second extension portion 148 may be received within the second recess 258, as shown in FIG. 2A. In this manner, the inflation port 154 may extend through the first recess 256, and the tether 156 may extend through the second recess 258. In some embodiments cross-sectional shapes of the recesses of the stabilizer body 230 may correspond to respective cross-sectional shapes of the mating portions of the external bolster. For example, when the stabilization device 202 is configured for use with the low-profile feeding device 100, the first recess 256 may have a C-shaped cross-sectional shape corresponding to a circular cross-sectional shape of the inflation port 154, and the second recess 258 may have a rectangular cross-sectional shape corresponding to a rectangular cross-sectional shape of the tether 156. It will be appreciated that the stabilizer body 230 may include any number of recesses arranged to correspond to the number and arrangement of extension portions of the external bolster of the low-profile feeding device, and that the cross-sectional shapes of the recesses may correspond to the respective cross-sectional shapes of the extension portions to provide a close fit between the mating surfaces.

In some embodiments, the stabilizer body 230 may include a slit 260 adapted to ease assembly of the stabilization device 202 with the low-profile feeding device. The slit 260 may extend from the opening 246 to the outer periphery of the stabilizer body 230. For example, the slit 260 may extend from the opening 246 to the second end 238 of the stabilizer body 230, as shown, although other arrangements of the slit 260 may be used. In this manner, the slit 260 of the stabilizer body 230 may be aligned with the slit 228 of the pad 210. As shown, the slit 260 also may extend from the first recess 256 to the top surface 232 of the stabilizer body 230, although other arrangements of the slit 260 may be used. During assembly, the slit 260 may allow the adjacent portions of the stabilizer body 230 to be separated from one another for positioning of the tube of the low-profile feeding device, such as the tube 110 of the feeding device 100, within the opening 246 of the stabilizer body 230 and then through the opening 226 of the pad 210. In this manner, the slit 228 of the pad 210 and the slit 260 of the stabilizer body 230 may allow the stabilization device 202 and the low-profile feeding device to be easily assembled with one another, while providing a close fit between mating features of the stabilizer body 230 and the external bolster of the low-profile feeding device (e.g., as shown in FIG. 2A). The stabilizer body 230 may be formed as a flexible structure having a high memory. In this manner, after separating the portions of the stabilizer body 230 adjacent the slit 260 for positioning the tube of the low-profile feeding device within the opening 246, such portions of the stabilizer body 230 may naturally return to their original position based on the memory of the material. In other words, at least a portion of the stabilizer body 230 may be resiliently deformable such that the portions of the stabilizer body 230 adjacent the slit 260 are configured to be resiliently deformed from a natural state to a deformed state (e.g., during assembly of the stabilization device 202 with the low-profile feeding device) and to automatically return to the natural state (e.g., due to the memory of the material). In some embodiments, the stabilizer body 230 may be formed of a polymeric material, although other suitable materials may be used. In some embodiments, the stabilizer body 230 may be formed of a transparent material or a translucent material, for example, to facilitate visualization of the low-profile feeding device and/or the ostomy site through the stabilizer body 230.

In some embodiments, as shown, the stabilizer body 230 may include a first half and a second half that are mirror images of one another. In other words, the stabilizer body 230 may be provided as a symmetric structure about a central plane of the stabilizer body 230. As shown in FIGS. 2D-2L, the stabilizer body 230 may include a first leg 270 and a second leg 272 that are spaced apart from one another by the cavity 244 and mirror images of one another. The first leg 270 may extend along the first side 240 of the stabilizer body 230, and the second leg 272 may extend along the second side 242 of the stabilizer body 230. As shown in FIG. 2A, the first leg 270 may be fixedly attached to the pad 210, and the second leg 272 may be fixedly attached to the pad 210. The stabilizer body 230 also may include a cross member 274 that extends between the first leg 270 and the second leg 272. The cross member 274 may be configured for extending over a portion of the external bolster. For example, when the stabilization device 202 is used with the low-profile feeding device 100, the cross member 274 may extend over part of the first extension portion 146, as shown in FIG. 2A. In some embodiments, the first leg 270, the second leg 272, and the cross member 274 may be integrally formed with one another. In other embodiments, the first leg 270, the second leg 272, and the cross member 274 may be separately formed and fixedly attached to one another. In some embodiments, the entirety of the stabilizer body 230 may be integrally formed as a unitary member. In other embodiments, two or more portions of the stabilizer body 230 may be separately formed and fixedly attached to one another. Various techniques of manufacturing the stabilizer body 230 may be used.

In some embodiments, the stabilizer body 230 may be provided with one or more viewing windows to allow visualization of the ostomy site of the patient during use of the stabilization device 202 with the low-profile feeding device. For example, the stabilizer body 230 may include a first window 280 extending from the cavity 244 to the first side 240 of the stabilizer body 230, and a second window 282 extending from the cavity 244 to the second side 242 of the stabilizer body 230. Each of the windows 280, 282 may be configured for allowing visualization of the ostomy site In some embodiments, as shown, each of the windows 280, 282 may be spaced apart from the opening 246. In other words, the first window 280 may be separated from the opening 246 by a portion of the stabilizer body 230, and the second window 282 similarly may be separated from the opening 246 by a portion of the stabilizer body 230. It will be appreciated that other arrangements of viewing windows may be used depending on the number and arrangement of the recesses of the stabilizer body 230.

Although specific embodiments of the disclosure have been described, one of ordinary skill in the art will recognize that numerous other modifications and alternative embodiments are within the scope of the disclosure. For example, while various illustrative implementations and structures have been described in accordance with embodiments of the disclosure, one of ordinary skill in the art will appreciate that numerous other modifications to the illustrative implementations and structures described herein are also within the scope of this disclosure.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments.

What is claimed is:

1. A feeding tube assembly for delivering fluids into a patient, the feeding tube assembly comprising:
   a pad configured for attaching to the patient, the pad comprising an opening extending from a top surface to a bottom surface of the pad;
   a low-profile feeding device comprising:
     a tube extending through the opening of the pad, the tube comprising a primary lumen;
     an external bolster fixedly attached to a proximal end portion of the tube and disposed adjacent to the top surface of the pad, the external bolster comprising an access port disposed along a top surface of the external bolster and in fluid communication with the primary lumen of the tube; and
     an internal bolster comprising an inflatable balloon fixedly attached to the tube and spaced apart from the external bolster; and
   a stabilizer body fixedly attached to the top surface of the pad and extending over the external bolster, the stabilizer body comprising:
     a cavity receiving a base portion of the external bolster therein;
     an opening extending from the cavity to a top surface of the stabilizer body and configured for allowing access to the access port; and
     a slit extending from the top surface toward a bottom surface of the stabilizer body and from the opening to a first end of the stabilizer body,
   wherein the external bolster further comprises:
     a tether extending away from the access port and through a first recess of the stabilizer body;
     a plug fixedly attached to the tether and configured for removably engaging the access port through the opening of the stabilizer body; and
     an inflation port extending away from the access port and through a second recess of the stabilizer body wherein the inflation port is in fluid communication with the inflatable balloon via a secondary lumen of the tube.

2. The feeding tube assembly of claim 1, wherein the pad further comprises an adhesive disposed on the bottom surface of the pad and configured for attaching the pad to the patient.

3. The feeding tube assembly of claim 1, wherein the pad further comprises a slit extending from the top surface to the bottom surface of the pad and from the opening to an outer periphery of the pad, and wherein the slit of the stabilizer body is aligned with the slit of the pad.

4. The feeding tube assembly of claim 1, wherein the stabilizer body is fixedly attached to the pad by an adhesive.

5. The feeding tube assembly of claim 1, wherein the tether has a rectangular cross-sectional shape, wherein the first recess of the stabilizer body has a rectangular cross-sectional shape, wherein the inflation port has a circular cross-sectional shape, and wherein the second recess of the stabilizer body has a C-shaped cross-sectional shape.

6. The feeding tube assembly of claim 1, wherein portions of the stabilizer body adjacent the slit of the stabilizer body are configured to be resiliently deformed from a natural state to a deformed state and to automatically return to the natural state.

7. The feeding tube assembly of claim 1, wherein the stabilizer body further comprises:
 a first window extending from the cavity to a first side of the stabilizer body and configured for allowing visualization of an ostomy site of the patient, the first window being spaced apart from the opening of the stabilizer body; and
 a second window extending from the cavity to an opposite second side of the stabilizer body and configured for allowing visualization of the ostomy site, the second window being spaced apart from the opening of the stabilizer body.

8. The feeding tube assembly of claim 1, wherein the stabilizer body further comprises:
 a first leg extending along a first side of the stabilizer body and fixedly attached to the pad;
 a second leg extending along an opposite second side of the stabilizer body and fixedly attached to the pad; and
 a cross member extending between the first leg and the second leg and over a portion of the external bolster;
 wherein the first leg and the second leg are spaced apart from one another by the cavity; and
 wherein the first leg, the second leg, and the cross member are integrally formed with one another.

9. A feeding tube assembly for delivering fluids into a patient, the feeding tube assembly comprising:
 a pad configured for attaching to the patient, the pad comprising an opening extending from a top surface to a bottom surface of the pad;
 a low-profile feeding device comprising:
  a tube extending through the opening of the pad, the tube comprising a primary lumen;
  an external bolster fixedly attached to a proximal end portion of the tube and disposed adjacent to the top surface of the pad, the external bolster comprising an access port disposed along a top surface of the external bolster and in fluid communication with the primary lumen of the tube; and
  an internal bolster fixedly attached to the tube and spaced apart from the external bolster; and
 a stabilizer body fixedly attached to the top surface of the pad and extending over the external bolster, the stabilizer body comprising:
  a cavity receiving a base portion of the external bolster therein, the cavity extending from the bottom surface of the stabilizer body to the opening of the stabilizer body;
  an opening extending from the cavity to a top surface of the stabilizer body and configured for allowing access to the access port; and
  a slit extending from the top surface toward a bottom surface of the stabilizer body and from the opening to a first end of the stabilizer body;
  a first recess receiving a first extension portion of the external bolster therein, the first recess extending from the bottom surface toward the top surface of the stabilizer body and from the cavity to the first end of the stabilizer body; and
  a second recess receiving a second extension portion of the external bolster therein, the second recess extending from the bottom surface toward the top surface of the stabilizer body and from the cavity to an opposite second end of the stabilizer body.

10. The feeding tube assembly of claim 9, wherein the slit of the stabilizer body extends from the first recess to the top surface of the stabilizer body.

11. A stabilization device for inhibiting movement of a low-profile feeding device relative to a patient, the low-profile feeding device having a tube, an external bolster, and an internal bolster, the stabilization device comprising:
 a pad configured for attaching to the patient, the pad comprising an opening extending from a top surface to a bottom surface of the pad and configured for receiving the tube therethrough; and
 a stabilizer body fixedly attached to the top surface of the pad and configured for extending over the external bolster, the stabilizer body comprising:
  a cavity configured for receiving a base portion of the external bolster therein, the cavity extending from the bottom surface of the stabilizer body to the opening of the stabilizer body;
  an opening extending from the cavity to a top surface of the stabilizer body and configured for allowing access to an access port of the external bolster;
  a slit extending from the top surface toward a bottom surface of the stabilizer body and from the opening to a first end of the stabilizer body;
  a first recess receiving a first extension portion of the external bolster therein, the first recess extending from the bottom surface toward the top surface of the stabilizer body and from the cavity to the first end of the stabilizer body; and
  a second recess receiving a second extension portion of the external bolster therein, the second recess extending from the bottom surface toward the top surface of the stabilizer body and from the cavity to an opposite second end of the stabilizer body.

12. The stabilization device of claim 11, wherein the pad further comprises an adhesive disposed on the bottom surface of the pad and configured for attaching the pad to the patient.

13. The stabilization device of claim 11, wherein the pad further comprises a slit extending from the top surface to the bottom surface of the pad and from the opening to an outer periphery of the pad, and wherein the slit of the stabilizer body is aligned with the slit of the pad.

14. The stabilization device of claim 11, wherein the stabilizer body is fixedly attached to the pad by an adhesive.

15. The stabilization device of claim 11, wherein the slit of the stabilizer body extends from the first recess to the top surface of the stabilizer body.

\* \* \* \* \*